(12) United States Patent
Jahn et al.

(10) Patent No.: US 10,182,910 B2
(45) Date of Patent: Jan. 22, 2019

(54) METHOD FOR FITTING AN IMPLANT TO A CATHETER

(71) Applicant: BIOTRONIK AG, Buelach (CH)

(72) Inventors: Andreas Jahn, Zurich (CH); Eugen Hofmann, Zurich (CH); Markus Hepke, Zurich (CH)

(73) Assignee: Biotronik AG, Buelach (CH)

( * ) Notice: Subject to any disclaimer, the term of this patent is extended or adjusted under 35 U.S.C. 154(b) by 716 days.

(21) Appl. No.: 14/508,120

(22) Filed: Oct. 7, 2014

(65) Prior Publication Data

US 2015/0107078 A1 Apr. 23, 2015

Related U.S. Application Data

(60) Provisional application No. 61/894,432, filed on Oct. 23, 2013.

(51) Int. Cl.
*A61F 2/24* (2006.01)
*A61F 2/95* (2013.01)

(52) U.S. Cl.
CPC .......... *A61F 2/2427* (2013.01); *A61F 2/2418* (2013.01); *A61F 2002/9522* (2013.01); *A61F 2230/005* (2013.01); *A61F 2230/0067* (2013.01); *Y10T 29/49826* (2015.01); *Y10T 29/53* (2015.01)

(58) Field of Classification Search
CPC ....... B25B 11/00; B25B 11/005; B25B 17/00; Y10T 29/49925; Y10T 29/49927; Y10T 29/53; Y10T 29/49826; B21D 39/04; B21D 39/046; A61F 2230/005; A61F 2/2427; A61F 2/2418; A61F 2002/9522

USPC .......................... 29/255, 270, 272, 515, 516
See application file for complete search history.

(56) References Cited

U.S. PATENT DOCUMENTS

| | | | | |
|---|---|---|---|---|
| 5,992,000 A | * | 11/1999 | Humphrey | A61F 2/958 29/282 |
| 6,387,117 B1 | * | 5/2002 | Arnold, Jr. | A61F 2/958 606/207 |
| 8,468,667 B2 | * | 6/2013 | Straubinger | A61F 2/2427 29/237 |
| 8,652,202 B2 | * | 2/2014 | Alon | A61F 2/2418 623/2.11 |
| 9,155,619 B2 | * | 10/2015 | Liu | A61F 2/0095 |
| 2005/0113804 A1 | * | 5/2005 | von Lehe | A61F 2/013 604/528 |
| 2006/0015136 A1 | * | 1/2006 | Besselink | A61F 2/013 606/200 |
| 2007/0079494 A1 | | 4/2007 | Serrano | |

(Continued)

FOREIGN PATENT DOCUMENTS

WO 2014085040 A1 6/2014

OTHER PUBLICATIONS

EP14188406.4 European Search Report dated Feb. 26, 2015.

*Primary Examiner* — Ryan J Walters
*Assistant Examiner* — Lawrence Averick
(74) *Attorney, Agent, or Firm* — Wagenknecht IP Law Group PC (57) ABSTRACT

A system and a method for crimping a heart valve prosthesis onto a catheter shaft. The system comprises two components (1, 2) which receive the heart valve prosthesis (12) and are inserted into one another in the direction (14) in order to crimp the heart valve prosthesis (12).

5 Claims, 5 Drawing Sheets

(56) References Cited

U.S. PATENT DOCUMENTS

| | | | |
|---|---|---|---|
| 2007/0288080 A1* | 12/2007 | Maccollum | A61F 2/82 623/1.11 |
| 2008/0221703 A1* | 9/2008 | Que | A61B 17/12022 623/23.65 |
| 2010/0043197 A1* | 2/2010 | Abbate | A61F 2/95 29/505 |
| 2013/0190859 A1* | 7/2013 | Hillukka | A61F 2/2427 623/2.11 |
| 2016/0287386 A1* | 10/2016 | Alon | A61F 2/2418 |

* cited by examiner

METHOD FOR FITTING AN IMPLANT TO A CATHETER

CROSS REFERENCE TO RELATED APPLICATIONS

This invention claims benefit of priority to U.S. provisional patent application Ser. No. 61/894,432, filed Oct. 23, 2014; the content of which is herein incorporated by reference in its entirety.

TECHNICAL FIELD

The invention relates to a method for fitting an intraluminal implant to a catheter shaft, wherein the diameter of the implant is reduced by a relative movement of at least two components, which each at least partially enclose a rotationally symmetrical space tapering along the axis of symmetry in one direction. The invention further relates to a system for carrying out the method.

BACKGROUND

Within the scope of the present invention, an intraluminal implant is understood to mean prostheses which are introduced into hollow organs of the body, where they remain or disintegrate or break down (degrade) after a predefined period of time. Intraluminal implants of this type are introduced by means of a catheter into the respective hollow organ. Intraluminal implants generally substantially have the shape of a tube and have a lattice structure, which corresponds to the dimension of the hollow organ into which the implants are introduced. Intraluminal implants that carry artificial heart valves are likewise known. An artificial heart valve of this type consists substantially of a flap formed of mostly biological tissue, which is secured in a lattice structure which carries the artificial heart valve. Artificial heart valves of this type can likewise be implanted by means of catheters at the location of the natural heart valve.

The present invention will be described hereinafter on the basis of the example of an artificial heart valve with a lattice structure (hereinafter: heart valve prosthesis), as is implanted at the location of the natural heart valve. The present invention is not limited however to this application, but is generally suitable for fitting intraluminal implants of the type described in the introduction to a catheter shaft.

A heart valve prosthesis of this type is implanted via a catheter. Here, the catheter is introduced for example via the artery in the groin, and the heart valve prosthesis is brought by means of the catheter to the site of implantation. There, the heart valve prosthesis unfolds and anchors in the vessel at the position of the natural heart valve. The natural heart valve is not removed here, but is merely displaced by the heart valve prosthesis.

For insertion by means of a catheter, the heart valve prosthesis has to be fitted appropriately to the shaft of the catheter for insertion of the heart valve prosthesis. Here, the diameter of the heart valve prosthesis has to be much smaller for insertion than at the site of implantation. The heart valve prosthesis is accordingly compressed ("crimped") onto the catheter shaft and is expanded at the site of implantation after insertion. Here, the expansion can occur in a self-expanding manner, as is the case with a stent, or by expansion of a balloon.

A method and a device for fitting a stent to a catheter shaft are described in U.S. Pat. No. 6,387,117. In accordance with the prior art described there, the stent is brought over the catheter shaft and is crimped by means of a press onto the catheter shaft. The press has at least two press dies, between which the catheter shaft with the stent is introduced. The press dies consist of a multiplicity of plates that have conical recesses and are arranged in parallel. The plates of the two dies are arranged here in an offset manner. The stent is accordingly pressed onto a catheter shaft by the adjacent conical recesses.

When fitting a heart valve prosthesis to a catheter shaft by a method according to the prior art, there is the risk that the heart valves consisting of biological tissue will tilt or bend. This would cause damage to the valves and would lead to a resultant malfunctioning, which is to be avoided at all costs.

SUMMARY

The object of the present invention is therefore to design a method and a system for fitting an intraluminal implant in such a way that the risk of damage to the intraluminal implant when fitting the implant to the catheter shaft is minimized. In particular, when fitting heart valve prostheses, a bending or tilting of the individual heart valves consisting of biological tissue is to be avoided.

The method according to the invention is characterized in that the at least two components carry out a relative movement along the longitudinal axis of the implant toward one another and into one another in such a way that the space enclosed jointly by the at least two components reduces, wherein the implant is located in the space enclosed jointly by the at least two components and is oriented in such a way that the longitudinal axis of the implant and the axes of symmetry of the rotationally symmetrical spaces are superimposed.

When fitting the intraluminal implant to the catheter shaft before implantation, the diameter of the implant has to be reduced. This requires a force that is directed perpendicularly onto the longitudinal axis of the generally rotationally symmetrical implant. In the prior art, this force is produced by a movement of components that is likewise oriented perpendicular to the longitudinal axis of the implant, such as the press from the prior art discussed beforehand. Here, two press parts are moved toward one another from above and below perpendicular to the longitudinal axis of the stent. The force is distributed merely tangentially at the periphery of the stent via the conical recesses in the press parts.

The present invention however generates the force for fitting and compressing the implant by means of a movement along the longitudinal axis of the intraluminal implant. Due to the inventive reduction of the rotationally symmetrical spaces formed and enclosed by the at least 2 components by means of a movement of the components toward one another and into one another along the longitudinal axis of the implant, the risk of damaging the intraluminal implant is considerably minimized.

Within the scope of this invention, a space enclosed by the component is understood to mean any space enclosed by the component as a result of the three-dimensional shaping of the component. For example, this space may be constituted by hollow spaces in a solid material element or spaces that are formed by a plurality of protruding shapings of the component. For example, a tubular element consisting of a lattice structure or bar structure would enclose a cylindrical space in its interior. This is analogous to an approximately cylindrical or truncated conical space, which encloses a bucket in its interior.

A rotationally symmetrical enclosed space is accordingly understood within the scope of this invention to mean an enclosed space that has an axis of symmetry about which the enclosed space can be rotated, without changing its shape. In the example of the tubular element, this is the cylinder axis, and in the example of the bucket, the central axis of the cylinder or of the truncated cone.

The components of the present invention each enclose at least partially a rotationally symmetrical space of this type, which tapers or reduces in a direction along the axis of symmetry or axis of rotation.

In accordance with the method according to the invention, the at least two components are accordingly moved toward one another and into one another in such a way that the space enclosed jointly thereby is reduced. The implant is located during this movement in the space enclosed jointly by the two components, and the two components move along the longitudinal axis of the implant. Here, the longitudinal axis of the implant lies over the axis of symmetry of the rotationally symmetrical spaces enclosed by the two components (longitudinal axis of the implant and axis of symmetry of the rotationally symmetrical space coincide).

Within the scope of this invention, the longitudinal axis of the intraluminal implant is understood to mean the central axis of the implant. The longitudinal axis of the intraluminal implant coincides accordingly with the axis of the catheter to which the intraluminal implant is fitted. In the case of an intraluminal implant that has substantially the shape of a tube, the longitudinal axis is accordingly the cylinder axis.

Within the scope of this invention, a catheter shaft is understood to mean at least the part of the catheter to which the intraluminal implant is fitted.

In a preferred embodiment of the invention, the implant is an artificial heart valve having a main body, in particular a self-expanding main body, or a stent, in particular a self-expanding stent. In this embodiment of the invention, the advantages of the invention are particularly relevant. In the case of a heart valve prosthesis, the valves are to open and close in order to enable or to stop a flow of blood. Here, the flow of blood, after implantation of the heart valve prosthesis, flows along the longitudinal axis of the heart valve prosthesis accordingly. The heart valves of the heart valve prosthesis accordingly fold toward this longitudinal axis or away therefrom. The longitudinal axis of the heart valve prosthesis is formed by the central axis of the main body that carries the valves. By fitting the heart valve prosthesis to the catheter shaft by means of a movement of the at least two components toward one another and into one another along this longitudinal axis of the heart valve prosthesis, the risk that the valves will bend away or tilt is considerably minimized. The movement of the components toward one another and into one another along the longitudinal axis corresponds to the possible movement of the valves, which fold toward the longitudinal axis or away therefrom. The risk is minimized accordingly, because, in accordance with the method according to the invention, the movement of the components during the fitting process corresponds to the movement of the heart valves during functioning.

The rotationally symmetrical space tapering along the axis of symmetry is advantageously a cone. The use of a conical enclosed space is particularly advantageous because a constant and tilt-free tapering of the enclosed space is thus ensured in a simple manner. In principle, other tapering rotationally symmetrical shapes, such as a pyramid or the like, are also conceivable however.

Within the scope of the application, a cone is understood to mean a cone or a truncated cone. In the case of a truncated cone, the tip of the cone is understood accordingly to mean the smaller area.

The conical spaces preferably move into one another in such a way that the space enclosed by at least two components becomes increasingly smaller. In this embodiment of the invention, at least two components are inserted into one another in such a way that the space enclosed by the two cones becomes increasingly smaller. The tips of the two cones are expediently oriented opposite one another and are arranged over the longitudinal axis of the intraluminal implant. Inserting the cones into one another thus continually reduces the diameter of the free space around the longitudinal axis of the implant enclosed by the cones of the at least two components.

A fluid flow, in particular a volume flow, is advantageously applied along the longitudinal axis of the implant at least during the movement of the at least two components toward one another and into one another. This embodiment is suitable in particular for fitting heart valve prostheses to a catheter shaft. In this embodiment of the invention, a fluid flow is applied along the longitudinal axis during the fitting process. This fluid flow ensures a pre-orientation of the heart valves, whereby the risk of the valves bending away or tilting is minimized further still.

In another embodiment of the invention, at least one component comprises a mandrel, which is oriented centrally in the space enclosed by the component in such a way that it is arranged over the longitudinal axis of the implant during the movement of the at least two components toward one another and into one another. This embodiment of the invention is likewise suitable in particular for the fitting of heart valve prostheses to a catheter shaft. In this embodiment of the invention, the mandrel ensures a pre-orientation of the heart valves. The components are guided into one another in this embodiment of the invention in such a way that the mandrel is guided into the heart valves of the heart valve prosthesis in the opening direction. The heart valves thus unfold cleanly and, after fitting of the prosthesis to the catheter shaft, can rest thereagainst.

With regard to the device, the stated object is achieved by a system for fitting an implant to a catheter shaft, said system comprising at least two components which each at least partially enclose a rotationally symmetrical space tapering along the axis of symmetry, and wherein at least one of the components, at the tapered end of the enclosed rotationally symmetrical space, has an opening that is suitable for the catheter shaft to be passed through.

The system according to the invention with an opening at the tapered end of the enclosed rotationally symmetrical space allows the method according to the invention to be carried out. The catheter shaft can pass through the opening at the tapered end of the rotationally symmetrical space. The movement of the at least two components toward one another and into one another along the longitudinal axis of the intraluminal implant is thus allowed. In the state fitted to the catheter shaft, the longitudinal axis of the intraluminal implant and catheter axis are superimposed. The catheter shaft with fitted implant can also be removed again from the inventive system through this opening.

The rotationally symmetrical space tapering along the axis of symmetry in one direction is expediently a cone. At least or two components preferably enclose a space which is formed by a cone and a cylinder. A cone, optionally in combination with a cylinder, is the simplest three-dimensional geometry for implementation of the invention. Components that enclose spaces of this type can be manufactured particularly easily. Depending on the specific shape of the intraluminal implant to be fitted, other shapes are also conceivable however within the scope of the invention.

Each of the at least two components particularly preferably has recesses, in which the other component(s) can engage. In this embodiment of the invention, the system consists of at least two, preferably two, components. Here, at least one of these components has recesses which can be filled with an accurate fit by shapings of the other component/components. Due to these recesses and corresponding complementary shapings, the components can be moved toward one another and into one another in a simple and guided manner Here, each component preferably has both recesses and shapings, which in each case correspond to another component. These mentioned embodiments ensure that identical intraluminal implants are always fitted in the same manner to identical catheter shafts. In addition, it is possible to ensure as a result of the shapings and corresponding recesses that the axes of symmetry of the components and the longitudinal axis of the implant are superimposed.

One component advantageously has a stop for the catheter shaft and/or one component has a receptacle for the implant. Here, the stop and receptacle may be in the same component or in two different components. The reproducibility is thus likewise improved, and the handling of the system according to the invention is simplified.

In another embodiment of the invention, at least one component has a mandrel which is oriented centrally in the space enclosed by the component and is arranged over the axis of symmetry of the rotationally symmetrical space. This mandrel, as already described with regard to the method, ensures an alignment of the heart valves with use of this embodiment of the system according to the invention for fitting heart valve prostheses to a catheter shaft.

An embodiment of the method according to the invention in combination with an embodiment of the system according to the invention will once more be described generally hereinafter.

In this embodiment, the system according to the invention consists of 2 components, which each enclose a conical space. The first component has a receptacle for the intraluminal implant and an opening at the tip of the enclosed conical space. The second component has a stop for the catheter shaft. The first component has recesses, which are shaped in such a way that they correspond to shapings of the second component.

The intraluminal implant is inserted into the receptacle of the first component, and the catheter shaft is guided through the opening in the tip of the conical component. The intraluminal implant and the catheter shaft are then located at least partially within the conical space, which is surrounded by the first component. Here, the catheter axis, longitudinal axis of the intraluminal implant, and longitudinal axis of the conical space are superimposed.

Both components are only moved toward one another along the catheter axis in such a way that the shapings of the second component engage in the recesses in the first component. Due to the further guided movement toward one another and into one another of the two components, the conical spaces enclosed by the components reduce. The intraluminal endoprosthesis and the catheter shaft are located in these conical spaces. The longitudinal axes of the conical spaces enclosed by the two components, the longitudinal axis of the intraluminal implant, and the catheter axis are superimposed. The space enclosed jointly by the two components thus reduces continuously and presses the intraluminal implant onto the catheter shaft until the stops at the recesses and/or for the catheter shaft are reached. The intraluminal implant is then pressed/fitted onto the catheter shaft, and the catheter shaft is removed with implant from the system via the opening in the first component. As the catheter shaft is removed from the component, the implant crimped on the catheter shaft is advantageously secured there by means of a tube, which is slid over the implant synchronously with the removal of the catheter shaft from the component.

This embodiment of the invention has been described here by way of example. Combinations of different embodiments described previously are easily possible for a person skilled in the art depending on the intraluminal implant to be fitted specifically and the specific catheter shaft.

The present invention provides a simple method and system for fitting an intraluminal implant onto a catheter shaft. The system can be easily handled and the embodiment of the method requires hardly any previous knowledge. The method according to the invention and the system according to the invention are suitable in particular for secure fitting of heart valve prostheses to a catheter shaft. The risk of the valves bending away or tilting when fitting the heart valve prosthesis to the catheter shaft is considerably minimized. The service life and functionality of the implant thus increase.

DESCRIPTION OF THE DRAWINGS

The invention will be explained in greater detail hereinafter on the basis of the exemplary embodiment of the invention illustrated in the figures, in which.

DETAILED DESCRIPTION

Figure 1:
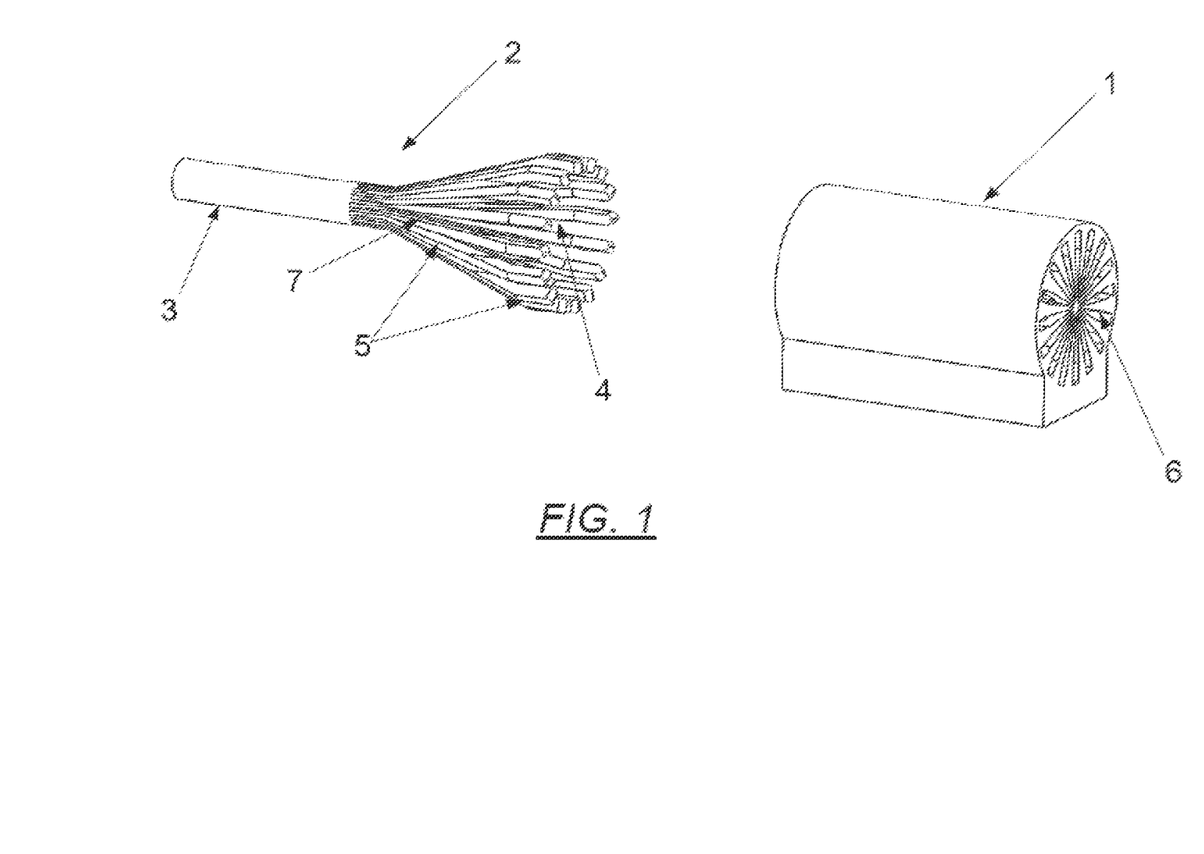
FIG. 1 shows an exemplary embodiment of the system according to the invention with two components, wherein both components are illustrated in the separated state.

The figures illustrate an exemplary embodiment of the system according to the invention, which consists of two components. FIG. 1 shows the two components 1 and 2 in the separated state, whereas in FIG. 2 the two components 1 and 2 have been moved into one another.

Figure 2:
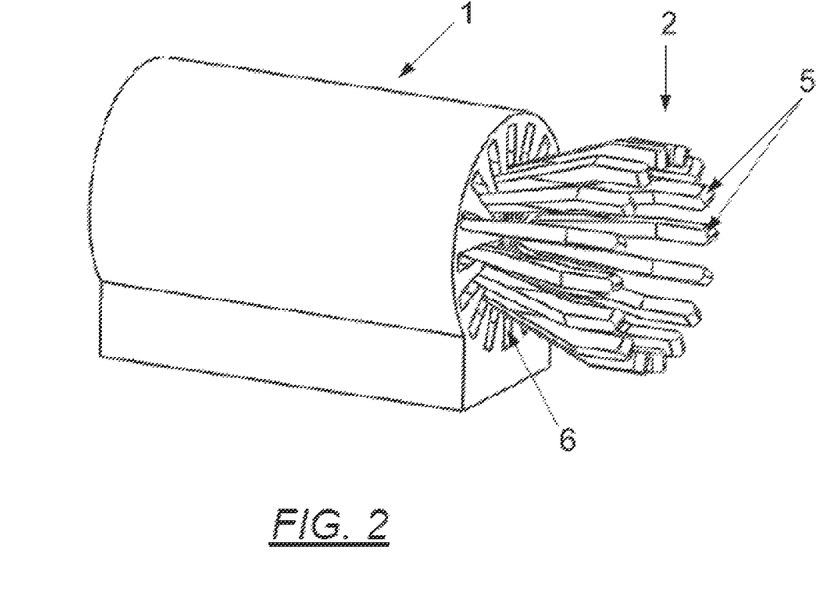
FIG. 2 shows the exemplary embodiment from FIG. 1 in the state in which both components are inserted fully into one another.

Component 1 is cylindrical and encloses, in the interior, a space which is formed from a cylinder and a cone (not illustrated in FIGS. 1-2). Component 2 consists of a grip 3 and shapings 5. A space is enclosed by the shapings 5 of the component 2 and is formed from a cylinder 4 and a cone 7. Component 1 has recesses 6, which are shaped in such a way that they can receive the shapings 5 of component 2.

As illustrated in FIG. 2, the components 1 and 2 can be moved toward one another and into one another, wherein the movement of the components 1 and 2 into one another is performed in a guided manner as a result of the recesses 6 in component 1 and the correspondingly shaped shapings 5 of component 2.

Both the cylindrical space 4 enclosed by the component 2 and the conical space 7 are rotationally symmetrical. The axis of symmetry runs through the central axis of the grip 3. The cylindrical space enclosed by the component 1 and the conical space enclosed by the component 1 (not illustrated in FIGS. 1-2) are likewise rotationally symmetrical, wherein the axis of symmetry here coincides with the central axis of the cylindrical component 1.

Figure 3A:
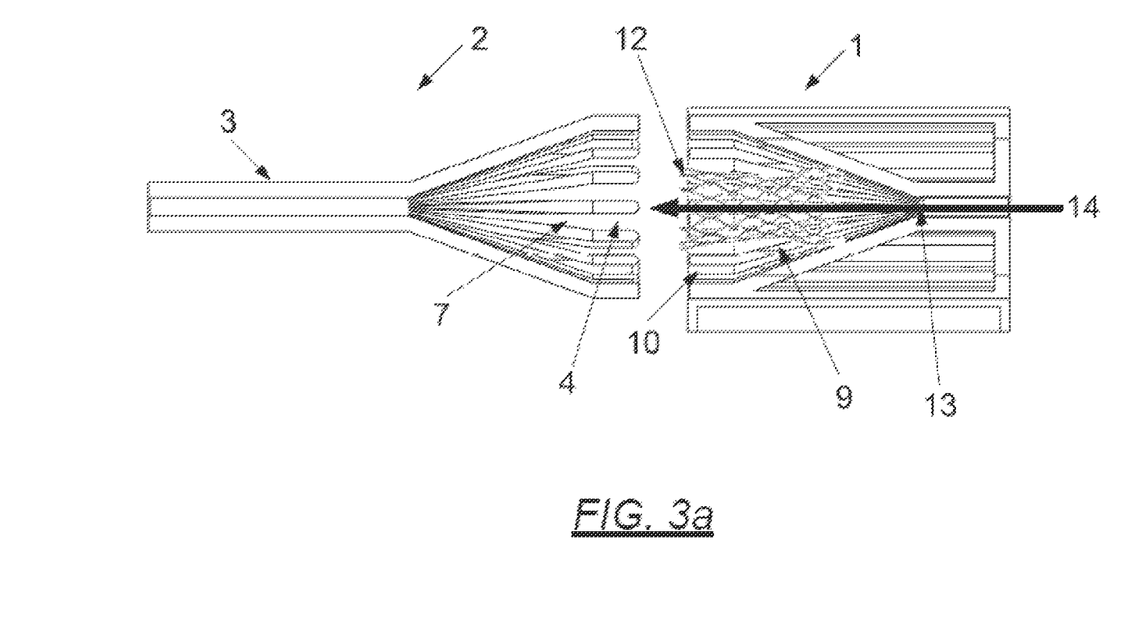
FIGS. 3a-c show an embodiment of the method according to the invention with the exemplary embodiment illustrated in FIGS. 1 and 2 of the system according to the invention.
Figure 3B:
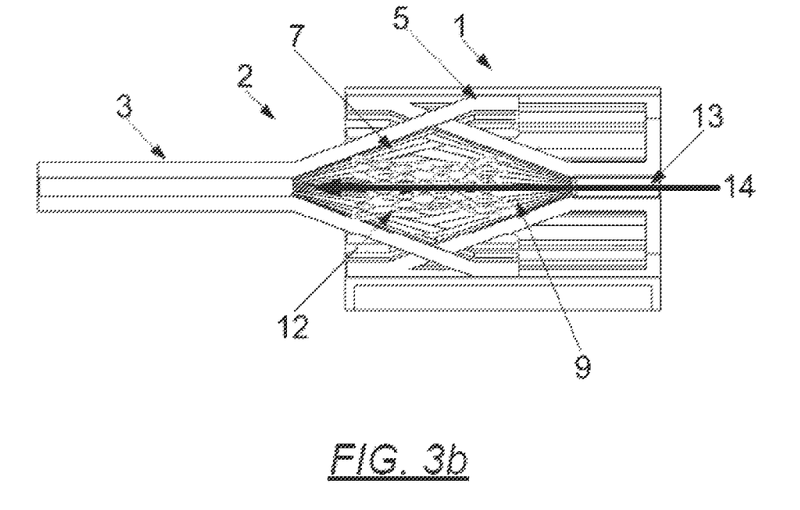
Figure 3C:
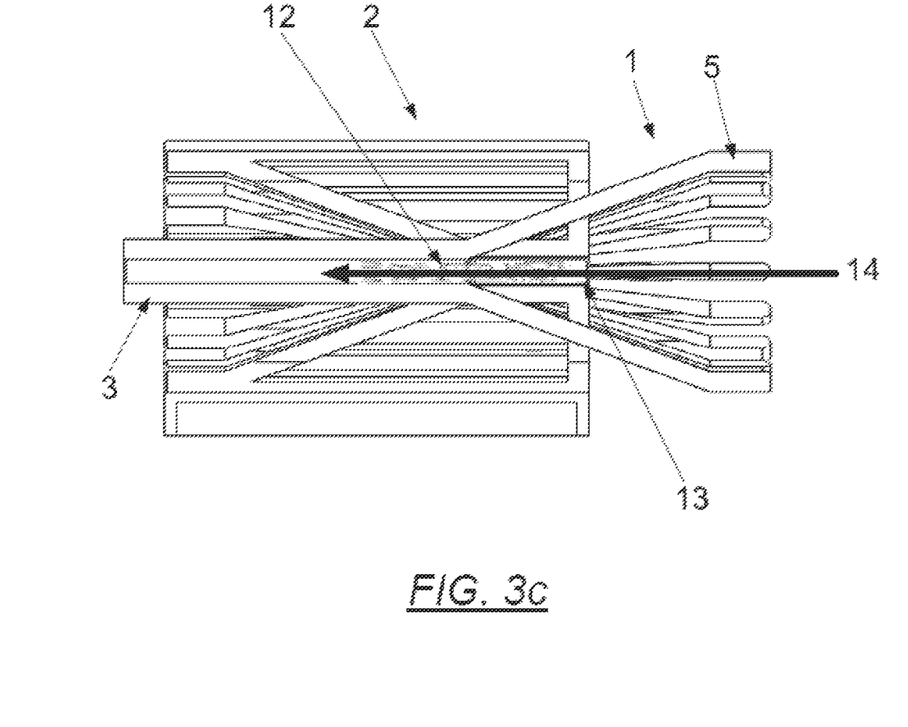

In FIGS. 3a to 3c, the two components 1, 2 from FIGS. 1 and 2 are each illustrated in section along the axis of symmetry. An exemplary embodiment of the method according to the invention for fitting an intraluminal implant 12 to a catheter shaft (not illustrated) will be described hereinafter with reference to FIGS. 3a-3c.

FIG. 3a shows the starting situation. The intraluminal implant, in this example a heart valve prosthesis 12, is positioned in component 1. The cylindrical space 10 enclosed by component 1 directly adjoins a conical space 9. A continuous opening 13, which reaches through component 1, is provided at the tip of the cone 9. The catheter shaft is inserted into the component 1 through this opening 13 along the arrow 14.

At the start of the method, the component 1 and component 2 are moved toward one another along the longitudinal axis of the heart valve prosthesis 12. The components 1, 2 are oriented and moved toward one another here such that the longitudinal axis of the heart valve prosthesis 12, longitudinal axis of components 1, 2, the axes of symmetry of the conical spaces 7, 9 enclosed by the components 1, 2, and cylindrical spaces 4, 10 and the catheter axis are superimposed and are oriented along the arrow 14.

FIG. 3b shows a method stage in which the two components 1 and 2 have already been moved into one another. At the moment shown in FIG. 3b, the space enclosed jointly by both components has already reduced. As the two components 1 and 2 moved toward one another in FIG. 3a, the space enclosed jointly by both components 1 and 2 comprised the cylindrical part 4 and the conical part 7 of component 2 and also the cylindrical part 10 and the conical part 9 of component 1. In the method stage of FIG. 3b, the space enclosed jointly by both components 1, 2 still only consists of the two conical parts 7 and 9.

The catheter shaft was advanced in FIG. 3b along the arrow 14 into component 2. The diameter of the heart valve prosthesis 12 has already reduced in FIG. 3b.

As can be seen in FIG. 3c, the space 7, 9 enclosed jointly by both components is continuously reduced until the heart valve prosthesis 12 is pressed and accordingly fitted onto the catheter shaft. The two components 1 and 2 are inserted here into one another as far as a stop (on the shaft 3, not illustrated). The catheter shaft with the heart valve prosthesis 12 fitted thereto is then removed from the system against the arrow 14. As the catheter shaft is removed, the heart valve prosthesis is secured on the shaft by means of a tube that is synchronously drawn over the heart valve prosthesis.

The system and the method according to the invention lead to movements in the direction 14 of the longitudinal axis of the heart valve prosthesis 12. The valve is thus nestled against the catheter shaft, and the risk of tilting or creasing of the valve is minimized.

In an embodiment of this exemplary embodiment, a volume flow can also additionally be introduced via the opening 13 or the shaft of the grip 3 and ensures a pre-orientation of the heart valve in the open position. The supply of the volume flow is dependent here on the orientation of the heart valve prosthesis 12 on the catheter.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A method of compressing an intraluminal implant for fitting to a catheter shaft, the method comprising:
    providing at least two components, each component comprising a rationally symmetrical space tapered along a longitudinal axis of symmetry,
    wherein the at least two components are tapered in opposite directions;
    positioning an intraluminal implant longitudinally within either of the spaces,
    wherein the implant is an artificial valve comprising a self-expanding main body or a self-expanding stent; and
    moving the at least two components into one another along the longitudinal axis in such a way that a space enclosed jointly by the least two components reduces while also flowing a fluid through the implant along the longitudinal axis thereby reducing the diameter of the implant.

2. The method as claimed in claim 1, wherein the rationally symmetrical space tapering along the axis of symmetry is a cone.

3. The method as claimed in claim 2, wherein conical spaces move into one another in such a way that the space enclosed by the least two components becomes increasingly smaller.

4. The method of claim 1, wherein a first of the at least two components comprises a plurality of recesses and a second of the at least two components comprises longitudinally extending finger shapings that fit longitudinally through the recesses during the movement.

5. A method of compressing an intraluminal implant for fitting to a catheter, the method comprising:
    providing at least two components, each component comprising a rotationally symmetrical space tapered in opposite directions along a longitudinal axis of symmetry;
    positioning an intraluminal implant longitudinally within either of the spaces, wherein the implant is an artificial valve comprising a self-expanding main body or a self-expanding stent; and
    moving the at least two components into one another along the longitudinal axis in such a way that a space enclosed jointly by the at least two components reduces while also flowing a fluid through the implant along the longitudinal axis thereby reducing the diameter of the implant;
    wherein at least one component has a mandrel which is oriented centrally in the space enclosed by the component in such a way the valves of the artificial heart valve rest against the mandrel during the movement of the at least two components into one another.

* * * * *